United States Patent [19]

Mittermeir et al.

[11] Patent Number: 5,556,410
[45] Date of Patent: Sep. 17, 1996

[54] SURGICAL NEEDLE WITH STRESS-RELOCATION MEANS

[75] Inventors: Werner Mittermeir, Prospect Heights, Ill.; Wayne J. Black, Vancouver, Wash.

[73] Assignee: M3 Systems, Inc., Northbrook, Ill.

[21] Appl. No.: 127,633

[22] Filed: Sep. 27, 1993

[51] Int. Cl.⁶ .................................................. A61B 17/34
[52] U.S. Cl. ............................................. 606/185; 604/264
[58] Field of Search ............................... 128/749–754; 604/164, 264; 606/1, 103, 127, 130, 139, 159

[56] References Cited

U.S. PATENT DOCUMENTS

| | | | |
|---|---|---|---|
| 4,616,656 | 10/1986 | Nicholson et al. | 128/630 |
| 4,790,329 | 12/1988 | Simon | 128/754 |
| 5,031,634 | 7/1991 | Simon | 128/754 |
| 5,056,523 | 10/1991 | Hotchkiss et al. | 606/130 |
| 5,127,916 | 7/1992 | Spencer et al. | 606/205 |
| 5,158,084 | 10/1992 | Ghiatas | 604/117 |
| 5,158,565 | 10/1992 | Marcadis et al. | 128/754 |
| 5,234,426 | 8/1993 | Rank et al. | 604/164 |

OTHER PUBLICATIONS

Advertisement for Kopans Breast Localization Needles By: Cook, Date: Unknown.
Advertisement for Sadowsky Breast Marking System By: Ranfac Corp., Date: 1985.
Advertisement for PercuGuide By: E–Z–EM, Date: Unknown.

*Primary Examiner*—Stephen C. Pellegrino
*Assistant Examiner*—Glenn Dawson
*Attorney, Agent, or Firm*—Dick and Harris

[57] ABSTRACT

A surgical needle including a cannula, hook-wire and reinforcement member for use in the manual location and marking of a lesion in a mass of soft tissue. The cannula rigidly supports the hook-wire during insertion into the soft tissue, and has a substantially cylindrical, hollow shaft and a cutting point located at an insertion end. The surgical needle further includes an anchor for restrainably locating the hook-wire proximate the lesion which is capable of springedly assuming a substantially acute angle relative to the remainder of the hook-wire. Reinforcement minimizes the potential for breakage of the hook-wire within the mass of soft tissue, after extension of the hook-wire beyond the insertion end of the cannula; in which the hook-wire is substantially D-shaped and closely approximates the diameter of the substantially cylindrical, hollow shaft; maximizing the structural size and integrity of the hook-wire to minimize the occurrence of breakage.

3 Claims, 2 Drawing Sheets

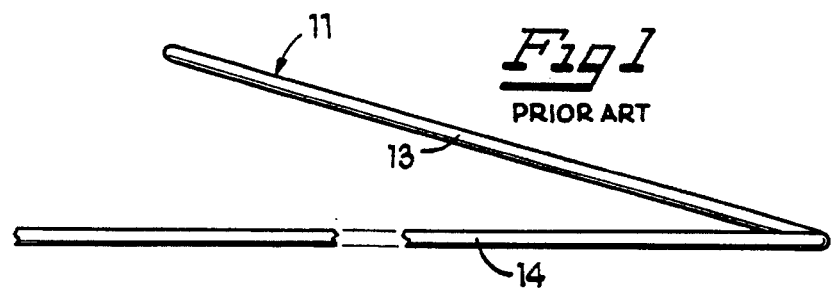
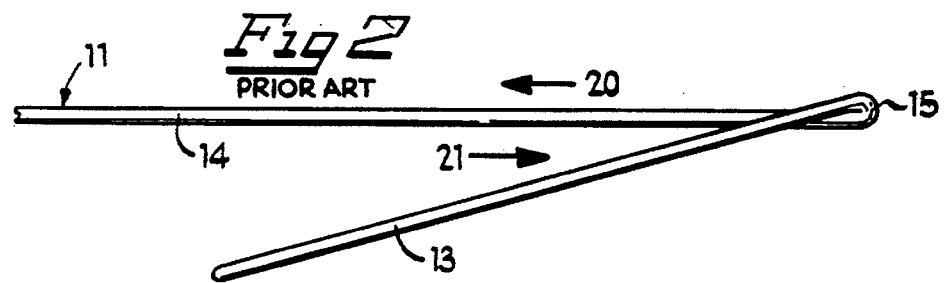
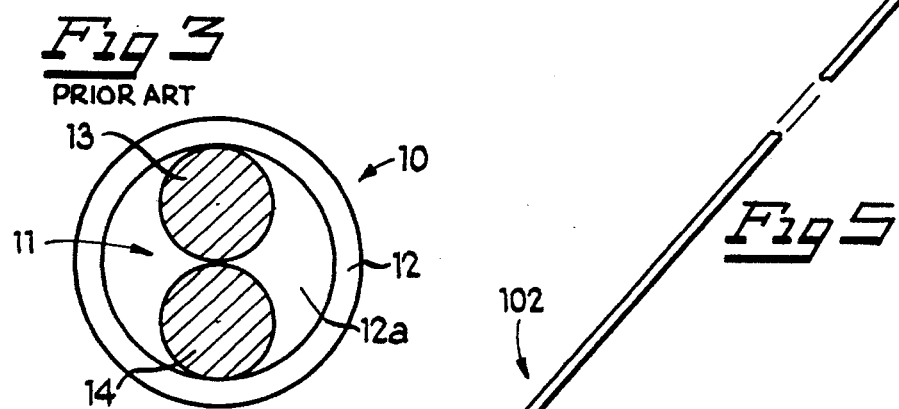
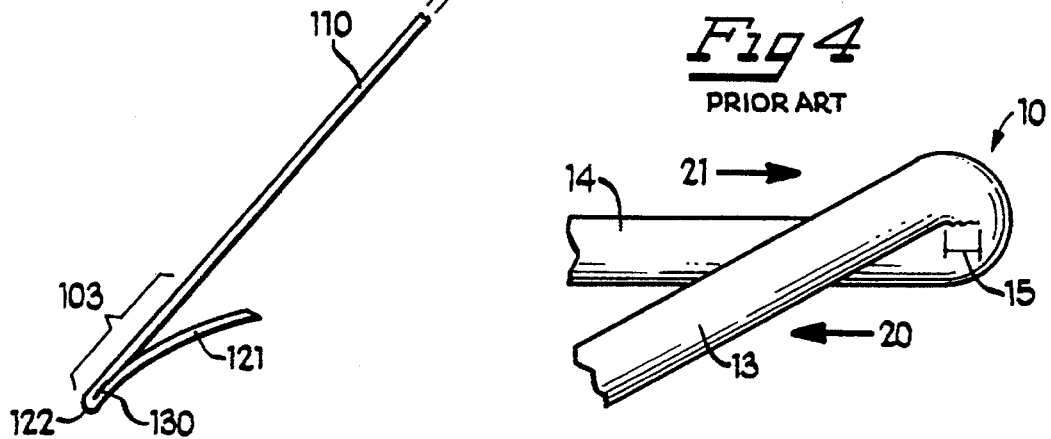

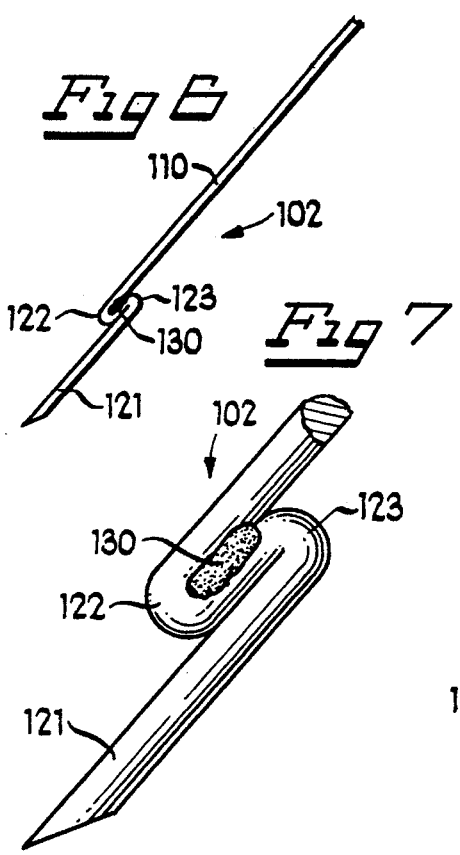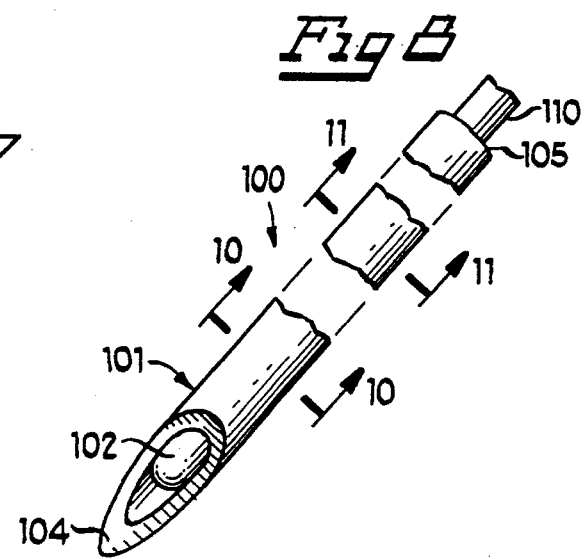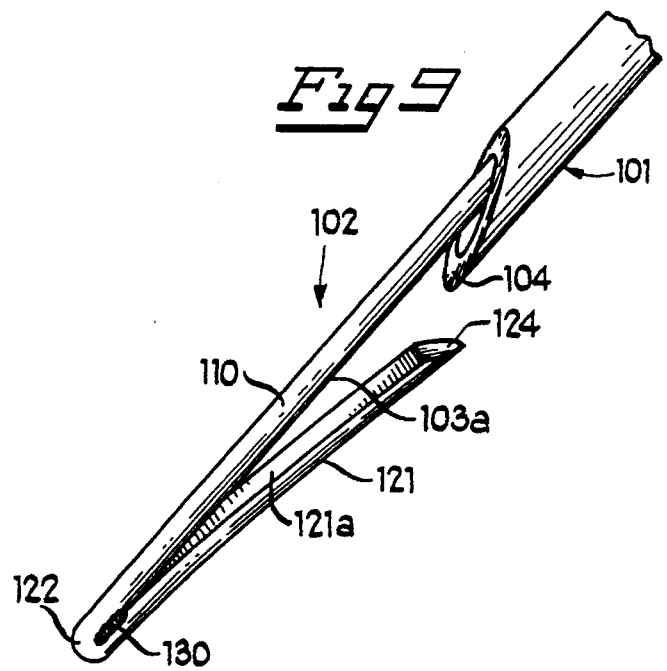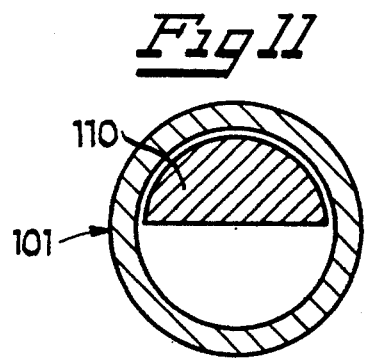

SURGICAL NEEDLE WITH STRESS-RELOCATION MEANS

BACKGROUND OF THE INVENTION

1. Field of the Invention

The present invention relates in general to surgical equipment and, in particular, to a surgical needle inserted into a mass of soft tissue for location and marking of a lesion using various radiographic techniques to later assist a doctor in locating the lesion during surgery.

2. Background Art

Localization needles have long been used in localizing and marking lesions in a mass of soft tissue, such as breasts, prostrates, livers, and muscle tissue to assist doctors in surgery (exploratory and otherwise). These localization needles are manually inserted into the mass of soft tissue while a doctor observes its location and progress through various radiographic techniques including, for instance, mammography, computerized tomography (CAT scan), fluoroscopy, standard x-ray, ultrasound and magnetic resonance imaging (MRI).

One type of needle, termed a "Kopans" needle, utilizes a single flexible hook-wire in marking the lesion. The hook-wire is introduced into the soft tissue sheathed within a rigid cannula. Once the localization needle is proximate the lesion, the doctor telescopically extends the flexible hook-wire out from the rigid cannula into the mass of soft tissue. A portion of the flexible hook-wire was previously fashioned into a hook, such that the hook-wire can be anchored proximate the lesion to aid in the location of the lesion during surgery. The exposed hook-wire is then often taped to the exposed skin of the patient.

Another type of localization needle is disclosed in U.S. Pat. No. 5,031,634 to Simon. Simon discloses a biopsy needle guide device containing two hook-wires within a cannula interconnected such that the hook-wires—which telescope through the side wall of the cannula, can be engaged and disengaged from the soft tissue to provide for readjustability. Each of the two hook-wires have D-shaped cross-sections, which together almost fill the cannula.

One shortcoming of the Kopans localization needle is its propensity to fracture while a doctor attempts to anchor it within the soft tissue. Such breakage results in a portion of the hook-wire remaining within the soft tissue, which then must be removed through difficult and costly surgery. Another shortcoming of the Kopans localization needle is the difficultly in locating the hook-wire during surgery due to its small diameter.

One further shortcoming of the prior art Simon needle is its non-severable construction, which forces the cannula to remain seated within the soft tissue unit completion of the surgical location process.

It is thus an object of the present invention to provide a surgical needle for the location and marking of lesion within a mass of soft tissue, which is reinforced so as to minimize the occurrence of breakage.

It is an associated object of the present invention to provide a more easily locatable hook-wire member to aid in location during surgery.

It is thus a further object of the present invention to provide a surgical needle having a removable cannula, which can be removed after location of the lesion with the soft tissue and deployment of the hook-wire—one which resists breakage typically occurring at the hook-wire fold-point These and other objects of the present invention will become apparent in light of the present specification, claims and drawings.

SUMMARY OF THE INVENTION

The present invention comprises a surgical needle for use in the manual location and marking of a lesion in a mass of soft tissue. The surgical needle comprises cannula means, hook-wire means, anchoring means and reinforcement means, which, in combination, substantially minimize the occurrence of breakage of the hook-wire means during insertion, anchoring and surgery.

The cannula means rigidly supports the hook-wire means during insertion and initial location of the surgical needle into and within the mass of soft tissue, providing a substantially cylindrical shaft with a substantially hollow void region, a cutting point located at an insertion end and a second end opposite said insertion end. The hook-wire means comprises a hook-wire member used for flexibly marking the lesion in the mass of soft tissue. The hook-wire means, which is initially positioned within the substantially cylindrical shaft of the cannula means, telescopically extends out of the cannula means at and beyond the insertion end. The cannula means is wholly removable from the mass of soft tissue and from the located hook-wire means following location and marking of the lesion by the hook-wire means.

The surgical needle further comprises anchoring means for restrainably locating the hook-wire member proximate the lesion in the mass of soft tissue. The anchoring means includes a hook member capable of springedly assuming a substantially acute angle relative to the remainder of the hook-wire member upon extension of the hook-wire means from the cannula means. Prior to extension, the hook member overlays at least a portion of the remainder of the hook-wire member which portion comprises a hook overlay region.

The surgical needle further includes reinforcement means for minimizing the potential for breakage of the hook-wire means within the mass of soft tissue after upon the hook-wire means being extended out of and beyond the insertion end of the cannula means. The reinforcement means are integrated into that portion of the hook member overlaying the hook-wire member and at least the hook overlay region of the hook-wire member.

In a preferred embodiment, the reinforcement means includes the hook-wire member and the hook overlay region each having a substantially D-shaped cross-section including a substantially flat side and a substantially cylindrical side opposite the substantially flat side. The substantially D-shaped cross-section serves to maximize the space which may be occupied simultaneously by the hook overlay region and the hook member within the substantially hollow void region prior to extension of the hook-wire means. In another preferred embodiment the entirety of the hook-wire means has a substantially D-shaped cross-section; substantially the same cross-sectional configuration as that of the hook-member and hook overlay region.

In this embodiment, the reinforcement means further includes the hook overlay region and hook member each having widths closely approximating the diameter of the substantially hollow void region, so as to further maximize the structural size and integrity of the hook overlay region and hook member to minimize the occurrence of breakage therebetween. In this embodiment, the hook member and hook overlay region each have their D-shaped cross-sections juxtaposed to one another at their respective flat sides prior to extension from the cannula means; further meeting at a fold-point projectable out of and beyond the insertion end of the cannula means.

In one embodiment of the surgical needle, the reinforcement means further comprises stress relocation means for relocating physical stress which may occur upon the exertion of forces along the hook-wire member. This stress relocation means is positioned proximate to but displaced away from the original, previously worked fold-point so as to further minimize the occurrence of breakage at the relatively fragile fold-point. In this embodiment, the stress relocation comprises a weld capable of bonding portions of the two overlapped D-shaped cross-sections to each other, thereby forming a region to accommodate the physical stresses at a position isolated from the fold-point.

In an alternative preferred embodiment, the reinforcement means solely comprises stress relocation means for relocating physical stresses which may occur upon the exertion of forces along the hook-wire member, to a position proximate to yet distanced from the fold-point. In this embodiment the hook-wire need not be of substantially D-shaped cross-section and thus, the stress relocation may be accomplished by welding portions of the hook-wire member to each other thereby forming a relocated region to accommodate the physical stresses isolated from the fold-point.

BRIEF DESCRIPTION OF THE DRAWINGS

FIG. 1 of the drawings is an elevated side view of a prior art Kopans biopsy localization needle;

FIG. 2 of the drawings is a top view of a prior art Kopans biopsy localization needle;

FIG. 3 of the drawings is a cross-sectional elevated front end view of a prior art Kopans biopsy needle illustrating the substantially cylindrical cross-sections of the hook-wire member which prevents the Kopans hook-wire from having a width closely approximating the diameter of the void region of the cannula;

FIG. 4 of the drawings is an enlarged fragmentary view of a prior art Kopans biopsy needle illustrating a stress fracture which may occur at the fold-point, on either the inside or outside of the fold-point, upon assertion of forces along the needle;

FIG. 5 of the drawings is an elevated side view of the hook-wire means of applicants' surgical needle showing, in particular, the hook member of the anchoring means assuming a substantially acute angle relative to the remainder of the hook-wire member, with relocation of the potential bend region away from the original hook fold-point;

FIG. 6 of the drawings is an enlarged elevated side view of the hook-wire means of applicants' surgical needle showing, in particular, the result of forces exerted along the hook-wire member, to prompt bending at a position displaced away from the fragile hook fold-point;

FIG. 7 of the drawings is an enlarged elevated side view of FIG. 6 showing, in particular, a weld capable of bonding portions of the hook member and hook overlay region, to create a new bending region to accommodate exerted stresses, one which is isolated from the fold-point;

FIG. 8 of the drawings is a bottom plan view of applicants' surgical needle showing, in particular, a portion of the cannula means having the hook-wire means partially enshrouded therein, prior to extension;

FIG. 9 of the drawings is an enlarged perspective view of applicants' surgical needle showing, in particular, the hook-wire means telescopically extending out of the cannula means at and beyond its insertion end;

FIG. 10 of the drawings is a front, cross-sectional view of applicants' surgical needle of FIG. 8 taken along line 10—10 and looking in the direction of the arrows, particularly, showing the substantially D-shaped cross-section of the hook member and hook overlay region in one preferred embodiment of the invention; and FIG. 11 of the drawings is a front, cross-sectional view of applicants' surgical needle of FIG. 8 taken along line 11—11 and looking in the direction of the arrows, particularly showing, the remainder of the hook-wire means as having a substantially D-shaped cross-section, with substantially the same width as the hook overlay region.

DETAILED DESCRIPTION OF THE DRAWINGS

While this invention is susceptible of embodiment in many different forms, several specific embodiments are shown in the drawings and will herein be described in detail, with the understanding that the present disclosure is to be considered as an exemplification of the principles of the present invention and is not intended to limit the invention to the embodiments illustrated.

A "Kopans" prior art surgical localization needle 10 is shown in FIGS. 1 through 4 of the drawings. The Kopans surgical localization needle 10 comprises flexible, cylindrical hook-wire 11 cannula 12 and hook portion 13. The hook is formed when portion 13 of hook-wire 11 is bent over portion 14 of hook-wire 11, which hook serves to restrainably locate hook-wire 11 within the mass of soft tissue. As described above, the Kopans surgical localization needle 10 is inserted into a mass of soft tissue with hook-wire 11 contained within cannula 12. Hook-wire 11 is capable of telescopic extension out of cannula 12, such that it can be restrainably located proximate a lesion within the mass of soft tissue. Due to the overlap of portions 13 and 14 of hook-wire 11 and the cylindrical cross-sections thereof, the diameter of hook-wire 11 must be sufficiently small such that both portions of hook-wire 11 can fit one on top of the other, within hollow shaft 12a of cannula 12. As can be seen with reference to FIG. 3, the small diameter required to fit hook-wire 11 within cannula 12 given its cylindrical cross-section results in a substantial amount of unutilized space within hollow shaft 12a of cannula 12. More importantly though, the small diameter makes hook-wire 11 more fragile and more difficult to electronically locate within the mass of soft tissue during surgery.

The hook in the Kopans localization needle 10 is often formed by bending portion 13 of hook-wire 11 over portion 14 of hook-wire 11 in a looping motion, such that there is substantial elliptical displacement between portion 13 and portion 14 of hook-wire 11 upon completion. The process of bending hook-wire 11 stresses, region 15, thus creating a weak "preworked" fragile area within hook-wire 11 where breakage would then be more apt to occur. This "looping" into the desired shape by cold working surgical stainless steel hook-wire 11, tends to prompt stress fracturing, as shown in FIG. 4, more at the folded region than at other locations along hook-wire 11. Due to the smaller diameter of cylindrical hook-wire 11, such that both components of it can fit within cannula 12 and the stress fracturing problem, the possibility of breakage due to torque or linear forces about fold region 15 increases; potentially resulting in portion 13 separating from portion 14 of hook-wire 11 within the mass of soft tissue.

After telescopic extension of hook-wire 11 out of cannula 12 and into the mass of soft tissue and removal of the cannula, the practitioner may pull on the external end of hook-wire 11 to restrainably locate hook-wire 11 proximate the lesion. The force created by the manual pulling of hook-wire 11 may be represented by arrow 20. Inasmuch as hook-wire 11 is surrounded by soft tissue during the assertion of force 20, the soft tissue will exert force 21 upon portion 13 of hook-wire 11. Force 21 can often result in further bending and elliptical displacement of portion 13 about region 15; with the resulting torque about region 15, in turn, causing a severing or fracture of portion 13 from portion 14 of hook-wire 11.

Applicants' surgical needle 100 is shown in FIGS. 5 through 11 of the drawings. Surgical needle 100, which is also used in the location and marking of a lesion in a mass of soft tissue, includes cannula means 101, hook-wire means 102, anchoring means 121 and reinforcement means. Surgical needle 100 is utilized by the doctor in the same manner described above, however, due to its structural features and mode of operation, the potential for breakage of hook-wire means 102 is substantially minimized and the ability to locate hook-wire means 102 within the mass soft tissue is increased.

As shown in FIGS. 8 and 9, cannula means 101, which rigidly supports hook-wire means 102, can be manually inserted into a mass of soft tissue. Cannula means 101 has a substantially cylindrical shaft with a substantially hollow void region, cutting point 104 located at the insertion end of cannula means 101 and a second end 105 opposite the insertion end. Cannula means 101, which in a preferred embodiment is fabricated of surgical stainless steel, is inserted into the mass of soft tissue with cutting point 104 leading the penetration.

During insertion, hook-wire means 102 is positioned within the cylindrical shaft of cannula means 101. Hook-wire means 102 flexibly marks the lesion in the mass of soft tissue under the guidance of a medical practitioner who views the progress of cannula means 101 (and hook-wire means 102 disposed therein) toward the lesion within the mass of soft tissue through various radiographic techniques. As cannula means 101 approaches and becomes proximate to the lesion, a doctor may telescopically extend hook-wire means 102 out of cannula means 101 at and beyond insertion end 104, thus locating and marking the lesion by hook-wire means 102. A doctor may then remove cannula means 101—which had served to rigidly support hook-wire means 102 during insertion into the mass of soft tissue and location therewithin—from the mass of soft tissue, thus leaving only hook-wire means 102 disposed within the mass of soft tissue. In a preferred embodiment, hook-wire means 102 will be of sufficient length such that a portion of hook-wire means 102 remains exposed outside the mass of soft tissue, and outside the patient. This exposed portion may be taped to the skin of the patient for stabilization.

Hook-wire means 102 comprises hook-wire member 110, preferably formed of surgical stainless steel, anchoring hook member 121, hook overlay region 103 and various reinforcement means. Anchoring means hook member 121, with hook point 124 restrainably locates hook-wire means 102 in the mass of soft tissue. Anchoring means hook member 121, which—upon extension of hook-wire means 102 from cannula means 101—is capable of springedly assuming a substantially acute angle relative to the remainder of hook-wire means 102, shown in FIGS. 5 through 9. Hook member 121 overlays at least a portion of the remainder of hook-wire member 110, at hook overlay region 103.

Surgical needle 100 further comprises reinforcement means which minimizes the potential for breakage of hook-wire means 102 within the mass of soft tissue after extension out of and beyond insertion end 104 of cannula means 101. The reinforcement means includes hook member 121 (overlaying hook overlay region 103) and hook overlay region 103 each having substantially D-shaped cross-sections as shown in FIGS. 9 through 11. As shown in FIGS. 9 and 10, the substantially D-shaped cross-sections of hook member 121 and hook overlay region 103 include substantially flat sides 121a and 103a respectively, with substantially cylindrical sides opposite thereto at 121b and 103b, respectively.

The substantially D-shaped cross-sections, as shown in FIG. 10, serve to maximize the space which may be occupied simultaneously by hook member 121 and hook overlay region 103 within the substantially hollow void region of cannula means 101. In FIG. 10, it can further be seen that due to the substantially D-shaped cross-section, the widths of hook member 121 and hook overlay region 103 may closely approximate the diameter of the substantially hollow void region of cannula means 101, so as to further maximize the structural size and integrity of at least hook member 121 and hook overlay region 103, if not the entirety of hook-wire means 102, thus minimizing the occurrence of breakage over the Kopans needle having cylindrical cross-section hook-wire 11 utilizing a smaller diameter wire 11, such that hook-wire 11 could fit within cannula 12.

In another preferred embodiment of surgical needle 100, the entirety of hook-wire means 102, including hook-wire member 110, has a substantially D-shaped cross-section, which may have the same width as hook overlay region 103 and hook member 121. However, given that the width constraint is determined by the simultaneous occupation of cannula means 101 by both hook member 121 and hook overlay region 103, hook-wire member 110, the portion of hook-wire means 102 extending beyond such portions, could also be cylindrical in cross-section.

In one preferred embodiment, the reinforcement means further comprises stress relocation means 130, comprising a bonding weld which relocates physical stress which may occur upon the assertion of forces along hook-wire means 102. As shown FIG. 7, stress relocation means 130 is positioned proximate to and extending from fold-point 122, between hook member 121 and hook overlay region 103, so as to further isolate any region where bending can occur, to minimize the occurrence of breakage at fold-point 122. Stress relocation means 130 functions such that if excessive forces are exerted upon hook-wire means 102, rather than prompt breakage at fragile fold-point 122 hook-wire means 102 may be bent back at region 123 not previously pre-worked to form a fold, as shown in FIGS. 6 and 7; thus preventing severing of a portion of hook-wire means 102.

In the preferred embodiment, stress relocation means 130 may comprise a weld between at least a portion of hook member 121 and hook overlay region 103 capable of bonding portions of overlapped substantially D-shaped cross-sections 121 and 103 to each other, thus protecting fold-point 122 by forming region 123 to accommodate the physical stresses, a region which is isolated from fold-point 122. Thus, any torque caused by a doctor anchoring hook-wire means 102 would occur at region 123, which never having been previously subjected to any type of cold worked or other bending, to render hook-wire means 102 capable of resisting more forces without fracturing.

In another embodiment, surgical needle 100 may have a hook-wire member of cylindrical cross-section, as in the prior art (shown in FIG. 3), but still have reinforcement means comprising stress relocation means 130. The inclusion of stress relocation means 130 would still substantially minimize the occurrence of breakage in surgical needle 100; even without components of the hook-wire member having substantially D-shaped cross-sections.

The foregoing description and drawings merely explain and illustrate the invention and the invention is not limited thereto except insofar as the appended claims are so limited, as those skilled in the art who have the disclosure before them will be able to make modifications and variations therein without departing from the scope of the invention.

What is claimed is:

1. A surgical needle for use in the location and marking of a lesion in a mass of soft tissue, said surgical needle comprising:

cannula means for manual insertion into the mass of soft tissue, said cannula means having a substantially cylindrical shaft defining a substantially hollow void region within said shaft, a cutting point located at an insertion end and a second end opposite said insertion end, said cannula means having a longitudinal axis;

hook-wire means positioned within said cylindrical shaft of said cannula means for flexibly marking the lesion in the mass of soft tissue, said hook-wire means including a hook-wire member;

said cannula means further serving to rigidly support said hook-wire means during insertion into the mass of soft tissue, said hook-wire means being capable of telescopically extending out of said cannula means at and beyond said insertion end;

said hook wire means further including anchoring means for restrainably locating said hook-wire member proximate the lesion in the mass of soft tissue, said anchoring means including a hook member, said hook member being capable of springedly assuming a substantially acute angle relative to said hook-wire member upon extension of said hook-wire means from said cannula means, said cannula means being wholly removable from said anchoring means following location and marking of the lesion by said hook-wire means;

said hook member overlaying at least a portion of said hook-wire member, said portion comprising a hook overlay region; and reinforcement means for minimizing the potential for breakage of said hook-wire means within the mass of soft tissue after extension out of and beyond said insertion end of said cannula means, said reinforcement means including said hook member and at least said hook overlay region of said hook-wire member, each having substantially D-shaped cross-sections including a substantially flat side and a substantially cylindrical side opposite said substantially flat side, said substantially D-shaped cross-sections serving to maximize that portion of said substantially hollow void region within said shaft, which may be occupied simultaneously by said hook overlay region and said hook member prior to said extension of said hook-wire means, said reinforcement means further including said hook overlay region and said hook member each having widths, defined at said substantially flat side of each and substantially perpendicular to said longitudinal axis, closely approximating the diameter of said substantially hollow void region, so as to further maximize the structural size and integrity of said hook overlay region and hook member, to minimize the occurrence of breakage therebetween, and said hook member and said hook overlay region, each having said D-shaped cross-sections juxtaposed to one another at their respective flat sides, prior to said extension, and further meeting at a fold-point projectable out of and beyond said insertion end of said cannula means.

2. The invention according to claim 1 wherein said reinforcement means further comprises stress relocation means for relocating physical stress which may occur upon the assertion of forces along said hook-wire member, to a position displaced from said fold-point, between said hook overlay region and hook member, so as to further minimize the occurrence of breakage at said fold-point.

3. The invention according to claim 2 wherein said stress relocation means comprises a weld bonding portions of said two overlapped D-shaped cross-sections of said hook overlay region and hook member to each other, thereby forming a region, to accommodate said physical stresses, isolated from said fold-point.

* * * * *